United States Patent
Sim et al.

(10) Patent No.: US 7,718,355 B2
(45) Date of Patent: May 18, 2010

(54) METHOD OF DETECTING PATHOGENIC MICROORGANISM IN REAL-TIME, USING MODIFIED FLOW-TYPE SURFACE PLASMON RESONANCE BIOSENSOR

(75) Inventors: Sang-jun Sim, Seoul (KR); Chang-deok Kang, Seoul (KR)

(73) Assignee: Sungkyunkwan University, Gyeonggi-Do (KR)

( * ) Notice: Subject to any disclaimer, the term of this patent is extended or adjusted under 35 U.S.C. 154(b) by 541 days.

(21) Appl. No.: 11/617,064

(22) Filed: Dec. 28, 2006

(65) Prior Publication Data

US 2007/0166703 A1    Jul. 19, 2007

(30) Foreign Application Priority Data

Dec. 29, 2005    (KR) ............... 10-2005-0133722

(51) Int. Cl.
*G01N 33/553*    (2006.01)
*G01N 33/569*    (2006.01)

(52) U.S. Cl. .................. 435/5; 435/7.2; 435/7.22; 435/7.32; 435/7.5; 436/524; 436/525; 436/164; 436/805

(58) Field of Classification Search ............ None
See application file for complete search history.

(56) References Cited

U.S. PATENT DOCUMENTS 5,965,456 A * 10/1999 Malmqvist et al. .......... 436/514
7,267,797 B1 * 9/2007 Craighead et al. ........ 422/82.05

OTHER PUBLICATIONS

Kang et al, "Performance enhancement of real-time detection of protozoan parasites . . . (SPR) biosensor", Enzyme and Microbiol Technology 39 (2006), pp. 387-390.*
Nice, E.C and B. Catimel. "Instrumental biosensors: new perspectives for the analysis of biomolecular interactions." BioEssays, 21.4, 1999, pp. 339-352.

* cited by examiner

*Primary Examiner*—Christopher L Chin
(74) *Attorney, Agent, or Firm*—Hamre, Schumann, Mueller & Larson, P.C.

(57) ABSTRACT

There is provided a method of detecting a pathogenic microorganism in real-time, using a modified flow-type surface plasmon resonance (SPR) biosensor, comprising the steps of: i) performing, in a batch-type, an immune reaction of a pathogenic microorganism and an antibody thereto; ii) selectively separating the pathogenic microorganism bound with the antibody; and iii) binding the pathogenic microorganism bound with the antibody on a surface of a chip of a flow-type SPR sensor system in real-time.

15 Claims, 3 Drawing Sheets

METHOD OF DETECTING PATHOGENIC MICROORGANISM IN REAL-TIME, USING MODIFIED FLOW-TYPE SURFACE PLASMON RESONANCE BIOSENSOR

BACKGROUND OF THE INVENTION

1. Technical Field

The present invention relates to a method of detecting a pathogenic microorganism in real-time, using a modified flow-type surface plasmon resonance (SPR) biosensor and, more particularly, to a method of detecting a pathogenic microorganism in real-time, using a modified flow-type SPR biosensor, which separates an immune reaction from surface binding reaction in a conventional flow-type SPR sensor, thereby increasing the limit of real-time detection of a pathogenic microorganism by the SPR sensor.

2. Discussion of Related Art

As industry has been developed, people have been exposed to a lot of environmental pollutions and have faced serious problems of health and sanitation. Among various environmental pollutions, the drink water pollution frequently causes infection accidents by pathogenic microorganisms.

Compared to those in the past, the infection accidents of waterborne epidemic have been significantly reduced. However, it is true that no country in the world eradicates the waterborne epidemic. The waterborne epidemic by the water pollution causes very serious troubles because it has harmful effects for a short period of time. While the water pollution by chemical materials causes a chronic disease which is long-lasting and recurrent, the water pollution by waterborne pathogen causes an acute disease to develop symptoms and results for a short period and to be likely to be spread by secondary infection. So, prevention is very important in the infection caused by waterborne pathogen. In this regard, if the presence of pathogenic microorganism in water is detected, waterborne diseases are expected to be prevented in advance.

Many methods of detecting and monitoring a pathogenic microorganism have been developed based on diverse application principles, such as the immunofluorescence assay, specifically, the enzyme-linked immunosorbent assay (ELISA), and the gene detection assay by amplifying the polymerase chain reaction (PCR). Some of products by the aforementioned methods have been commercialized. However, among the methods of detecting a pathogenic microorganism, the aforementioned assays have a relatively high detecting ability but have drawbacks in that a sample needs to be pretreated and it takes a long time for an immune reaction. Accordingly, a new sensor for detecting a pathogenic microorganism needs to be developed.

To solve the drawbacks of conventional sensors for detecting a pathogenic microorganism, many researchers have been actively developing sensors for detecting pathogenic microorganisms, using a surface plasmon resonance (SPR) system which is capable of detecting a pathogenic microorganism in real-time and has the function of a label-free sensor.

Specifically, the technique of an SPR sensor is widely used as a biosensor and/or biochip measurement method, by signal changes occurring when biological materials, such as proteins, are bound with the surface of the sensor (Literature: Nice, E. C. and Catimel, B., BioEssay, 1999, 21, 339-352). The surface plasmon is a quantized oscillation of a free electron which is propagated along a conductive surface, such as a metal surface. The surface plasmon is excited by light which passes a dielectric medium, such as a prism, and then which is incident upon a metal thin film at an angle being same as or greater than a critical angle of the dielectric medium. Then, the surface plasmon generates resonance at a predetermined angle. An angle of incidence at which the SPR is generated, that is, an angle of resonance, is sensitive to a change in the index of refraction of a material being close to the metal thin film. The SPR sensor with the above-described feature is used for quantitative analysis, qualitative analysis and measurement of the thickness of a sample, by the change in the index of refraction of a material (that is, the sample) being close to the metal thin film. Compared to conventional immunoassays, the SPR sensor has several merits as follows:

First, in terms of specificity, a conventional immunoassay needs to use a specific label material (a luminous substance or a fluorescent substance) or a secondary antibody for measurement, thereby changing the activity or original properties of the sample to be measured. However, since an SPR sensor does not require for any label of a specific material or any pretreatment of the sample, it measures the sample while maintaining the original properties of the sample.

Second, in terms of sensitivity, a conventional immunoassay has the limit of detection which is generally from several tens of ng unit to several ug unit as for proteins. However, a SPR sensor is capable of detection to several pg unit, thereby having high sensitivity.

Third, in terms of time for measurement, a conventional immunoassay obtains a measurement result after several hours starting from the pretreatment of the sample, if short, or several days, if long. However, a SPR sensor does not need any special pretreatment of the sample, so that it has the promptness to obtain a measurement result within several minutes to several tens of minutes.

Last, in terms of simplicity of analysis procedure, a general immunoassay needs highly skilled personnel and includes a complicated pretreatment process of the sample for experimental procedure reasons. However, a SPR sensor obtains a measurement result by only injecting the sample on the surface of a sensor chip, so that it has the simplified analysis procedure, compared to the conventional immunoassay.

However, unlike an inter-immune reaction between proteins, an immune reaction to detect a pathogenic microorganism is slow in an immune reaction speed. In the immune reaction, detection signals are weakly measured due to the signal amplification characteristics of the SPR. Accordingly, it is difficult to use the SPR sensor to detect a pathogenic microorganism as a sensor for detecting a pathogenic microorganism, by applying a flow-type method like a conventional SPR sensor for detecting proteins.

Most of the conventional SPR sensors for detecting a pathogenic microorganism apply a batch-type method not a flow-type method. When using the batch-type sensors, it is difficult to realize the promptness of detection, which is one of the merits of the aforementioned SPR sensor.

Accordingly, a method of detecting a pathogenic microorganism in real-time, using a modified flow-type SPR sensor system is provided, in order that the conventional SPR sensor for detecting a pathogenic microorganism is used, with the promptness of detection, as a SPR sensor for detecting a pathogenic microorganism in real-time.

SUMMARY OF THE INVENTION

Therefore, the present invention is directed to provide a method of detecting a pathogenic microorganism in real-time, using a modified flow-type surface plasmon resonance (SPR) biosensor.

In accordance with an embodiment of the present invention, the present invention provides a method of detecting a pathogenic microorganism in real-time, using a modified flow-type SPR biosensor, comprising: i) performing, in a batch type, an immune reaction of a pathogenic microorganism and an antibody thereto; ii) selectively separating the pathogenic microorganism bound with the antibody; and iii) binding the pathogenic microorganism bound with the antibody on a chip of a flow-type SPR sensor system.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

The present invention will now be described more fully hereinafter with reference to the accompanying drawings, in which a preferred embodiment(s) of the invention is shown.

The present invention relates to a method for detecting a pathogenic microorganism in real-time, using a modified flow-type surface plasmon resonance (SPR) biosensor. To detect a pathogenic microorganism, the present invention applies the non-labeled real-time detection which is the most significant characteristic and merit of an SPR sensor, based on a flow-type SPR sensor system. Although the flow-type SPR sensor in detecting a microorganism has the merit of non-labeled real-time detection, it has the drawbacks of the limit of detection or measurement of a pathogenic microorganism due to its own measurement principles, compared to the other sensors for detecting pathogenic microorganisms. That is, unlike a general inter-immune reaction between proteins, an immune reaction between a pathogenic microorganism and an antibody thereto is slow in the immune reaction speed, and detection signals are weakly measured due to the signal amplification characteristic of SPR. Thus, the SPR sensor has a difficulty in being used as a sensor for detecting a pathogenic microorganism, by applying a flow-type method, as in a conventional SPR sensor for detecting a protein. The present invention solves the above described problem of the flow-type SPR sensor and provides a method of detecting a pathogenic microorganism in real-time, using a modified flow-type SPR biosensor, which enhances the efficiency in the immune reaction of the pathogenic microorganism and the efficiency in binding on a chip surface.

Figure 1A:
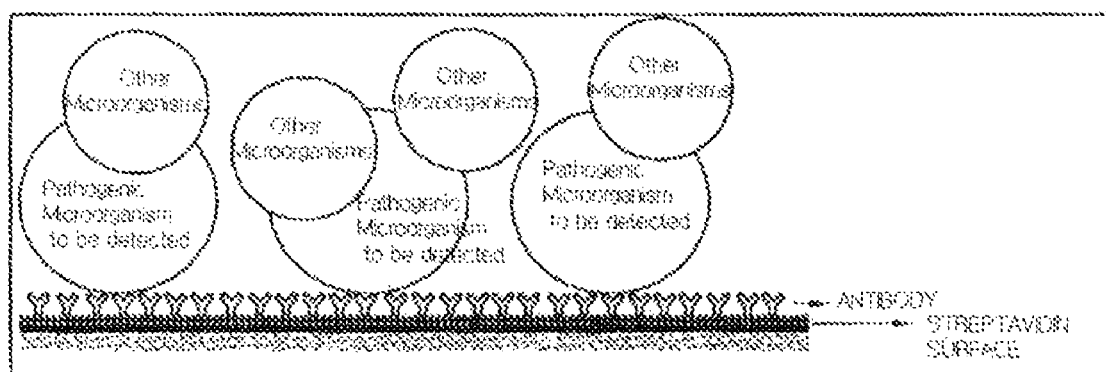
FIG. 1A is a view illustrating the concept of a conventional flow-type surface plasmon resonance (SPR) biosensor for detecting a pathogenic microorganism.

FIG. 1A illustrates the constitution of a general flow-type SPR biosensor system for detecting a pathogenic microorganism. As illustrated in FIG. 1A, an optimum ligand is formed on the surface of a chip with a gold thin film for SPR measurement. An antibody with peculiar immune reactivity to a pathogenic microorganism is fixed to the ligand, to form a final surface. A sample including the microorganism is continuously injected in a flow-type, so that, while the sample passes the chip surface, the immune reaction occurs between the antibody on the chip surface and an antigen on the cell surface of the pathogenic microorganism included in the sample, and the pathogenic microorganisms are bound on the chip surface by an antigen-antibody binding. Then, an SPR signal (RU value) increases, and the microorganism is detected by amplifying the SPR signal. However, in this process, since the size of the pathogenic microorganism included in the sample is relatively larger than the antibody fixed on the chip surface, the efficiency of binding the microorganism and the antibody by the immune reaction in the fluid flow of the SPR system is low. Consequently, the limit of detection of the pathogenic microorganism is formed at a high level, due to the inefficient immune reaction and the surface fixation.

Figure 1B:
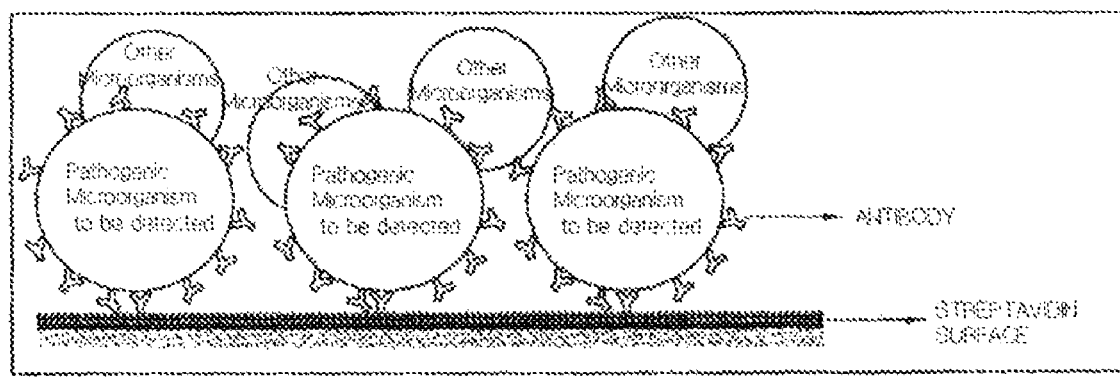
FIG. 1B is a view illustrating the concept of a modified flow-type SPR biosensor for detecting a pathogenic microorganism according to the present invention.

To solve the structural problem of the conventional flow-type SPR sensor, the present invention provides a method of detecting a pathogenic microorganism, using a modified flow-type SPR biosensor system as illustrated in FIG. 1B. According to the method, the immune reaction between an antibody and a pathogenic microorganism is separately performed from the fixation of the microorganism on an SPR chip. That is, the immune reaction of the pathogenic microorganism and the antibody, which has been performed within a moving flow, is performed, in the batch type, within a test tube for a short time of about ten minutes. The pathogenic microorganism bound with the antibody is selectively separated, using a cut-off membrane filter. The pathogenic microorganism bound with the antibody is bound, in real-time, on the chip of the flow-type SPR system. Finally, the pathogenic microorganism is detected by a detection signal of the sample.

In accordance with another embodiment of the present invention, a peculiar antibody to the pathogenic microorganism is bound with biotin. The pathogenic microorganism bound with the antibody is selectively separated using the cut-off membrane filter. Streptavidin is continuously injected to form a streptavidin layer on the chip surface of the flow-type SPR system. The pathogenic microorganism bound with the antibody is bound on the streptavidin chip surface of the flow-type SPR system, by a biotin-streptavidin reaction. The biotin-streptavidin binding is a typical material pair which is well known as having high binding affinity and is widely used in many biological analyses. That is, in the flow-type SPR system which has the fixation of the microorganism by the relatively slow immune reaction, the SPR signals generated on the chip are continuously collected in real-time to be used as the detection signals of the pathogenic microorganism, by using the biotin-streptavidin binding with the high affinity. This method enhances the efficiency of fixation of the microorganism on the SPR chip surface and consequently obtains the SPR signals being significantly increased.

In accordance with another embodiment of the present invention, the conditions of the immune reaction and the conditions of the cut-off membrane filter may be changed, depending on a pathogenic microorganism to be detected.

In accordance with another embodiment of the present invention, a waterborne pathogen is detected in real-time, using the modified flow-type SPR biosensor. The waterborne pathogen includes a *cryptosporidium parvum* virus.

In accordance with another embodiment of the present invention, a pathogenic virus is detected in real-time, using the modified flow-type SPR biosensor. The pathogenic virus may be selected from any one of the group of a herpes virus, a pox virus, a hepatitis virus, a picorna virus, a rota virus, an influenza virus, a paramyxo virus, a rubella virus, a rabies virus, a slow virus, an onco virus, and an HIV virus.

In accordance with another embodiment of the present invention, the number of microorganisms may be quantified, using the modified flow-type SPR biosensor.

In accordance with another embodiment of the present invention, a self assembled monolayer of a thiol terminated group (—SH) is formed on the surface of the chip with the gold thin film for the SPR measurement, which is used in the aforementioned flow-type and modified flow-type SPR biosensor systems for detecting the aforementioned pathogenic microorganism; and a ligand material (specifically, streptavidin) which is capable of binding bio-related molecular materials, such as an antibody or an object to be detected, may be fixed on the self assembled monolayer.

Below, a preferred exemplary embodiment of the present invention and a comparative example will be described. However, the present invention may, however, be embodied in different forms and should not be construed as limited to the embodiment set forth herein.

Exemplary Embodiment

Among many pathogenic microorganisms, specifically, a *cryptosporidium parvum* is converted into the form of an oocyst even through a disinfection process upon purifying water, so that it has high resistance to disinfection. Since the *cryptosporidium parvum* is considered as a waterborne virus which requires for more thorough water-purity control, it is selected as an object to be detected in the preferred embodiment of the present invention.

The surface of the chip with the gold thin-film for the SPR measurement, which is used in the modified flow-type SPR biosensor system for detecting a pathogenic microorganism as illustrated in FIG. 1B, is manufactured by forming a self assembled monolayer, using an admixed alkanethiol solution. The chip manufactured in this manner is placed in the flow-type SPR sensor system.

Samples of the *cryptosporidium parvum* oocysts are respectively prepared in the concentrations of $10^2$ oocysts per Ml, $10^3$ oocysts per Ml, $10^4$ oocysts per Ml, and $10^6$ oocysts per Ml. Each sample is cultivated in the environment of 37° C. for thirty minutes, to perform an immune reaction between each sample and the *cryptosporidium* antibody (manufactured by Waterborne Inc., USA). The *cryptosporidium* antibody is the antibody bound with biotin. After the immune reaction is completed, the samples are centrifugally separated for five minutes, using a cut-off membrane filter with an opening being 0.2 µm in size. Then, the antibodies which are not related to the immune reaction are removed, and only the *cryptosporidium* cells with the biotin-antibody binding are obtained.

Figure 2:
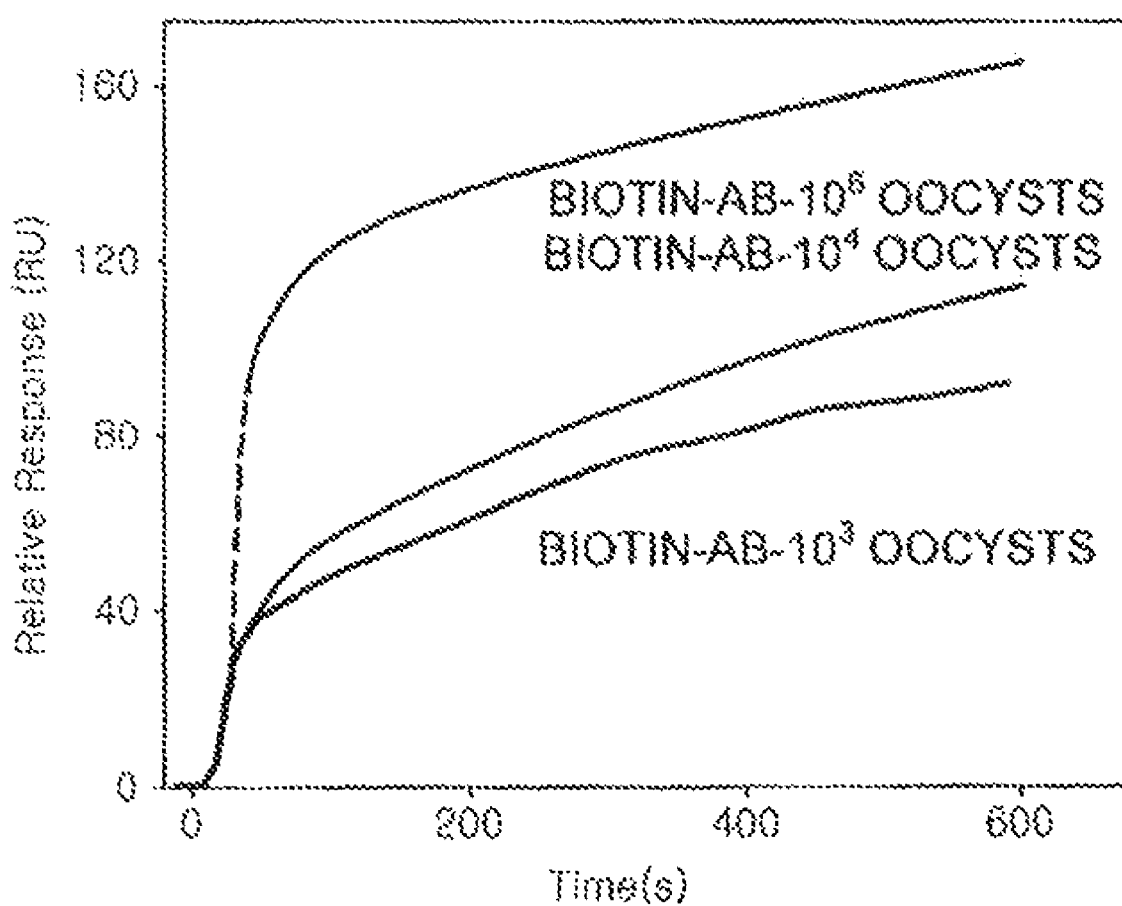
FIG. 2 is a graph illustrating a result of detecting a virus, using the modified flow-type SPR biosensor according to the present invention by changes in SPR sensorgram, to detect, in real-time, *cryptosporidium parvum* oocyst which is a waterborne pathogen.
Figure 3:
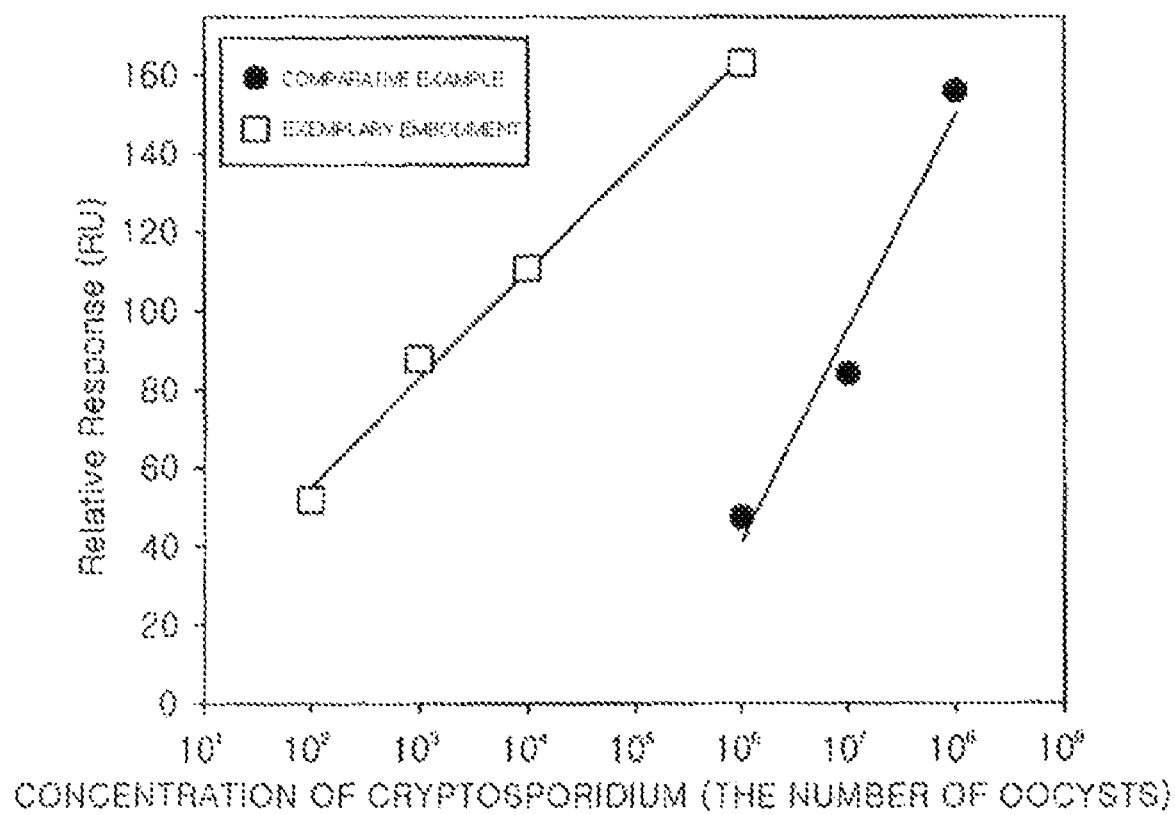
FIG. 3 is a graph comparatively illustrating the limits of detection of the conventional flow-type SPR biosensor and the modified flow-type SPR biosensor according to the present invention, upon detecting, in real-time, the *cryptosporidium parvum* oocyst which is a waterborne pathogen.

To detect the *cryptosporidium* cells completing the immune reaction, using the flow-type SPR sensor system, streptavidin which is the ligand of biotin is fixed in the flow-type SPR sensor system. Streptavidin is injected for fourteen minutes, at the speed of 5 µl/min, to be fixed on the surface of the chip. The *cryptosporidium* samples with the biotin-antibody binding are injected on the surface where streptavidin is effectively formed, for ten minutes, at the speed of 2 µl/min, to induce the binding on the chip surface. Then, the detection of the *cryptosporidium* cells is checked through the SPR signals being obtained (as illustrated in FIG. 2) and the quantification thereof is realized (as illustrated in FIG. 3).

Comparative Example

A flow-type SPR biosensor system for detecting a pathogenic microorganism (as illustrated in FIG. 1A) is used to detect *cryptosporidium* cells. The formation of the surface of the chip with the gold thin film used in the SPR system and the method of positioning the chip are same as the above-described Exemplary Embodiment. Samples of the *cryptosporidium parvum* oocysts to be used in the comparative experiment are respectively prepared in the concentrations of $10^6$ oocysts per Ml, $10^7$ oocysts per Ml, and $10^8$ oocysts per Ml. The *cryptosporidium* antibody used for the immune reaction is the same as used in Exemplary Embodiment.

To detect the *cryptosporidium* cells through the immune reaction with the *cryptosporidium* antibody, using the flow-type SPR sensor system, the surface including streptavidin which is the ligand of the antibody bound with biotin is fixed in the flow-type system, in the same manner as Exemplary Embodiment. The biotin-antibody is injected for ten minutes, at the speed of 5 µl/min, to be fixed on the surface where streptavidin is effectively formed. The *cryptosporidium* samples prepared in the respective concentrations are injected for ten minutes, at the speed of 2 µl/min, to induce the immune binding on the chip surface. Then, the detecting ability of the *cryptosporidium* cells is analyzed through the SPR signals being obtained (as illustrated in FIG. 3).

FIG. 3 shows the results of detecting the *cryptosporidium* cells according to Exemplary Embodiment and Comparative Example respectively. When the *cryptosporidium* cells are detected in real-time, using the SPR sensor systems, the modified flow-type SPR sensor system according to the present invention significantly increases the detecting ability of the *cryptosporidium* cells, compared to the conventional flow-type SPR sensor system which is widely used for protein analysis. Further, the method of detecting a pathogenic microorganism according to the present invention indicates the same detecting ability as that of a batch-type SPR sensor for detecting a microorganism, and maintains the merits of the merits of the above-described flow-type SPR sensor system.

As described above, the present invention provides the non-labeled real-time detection method for pathogenic microorganism, and significantly improves a detecting ability of waterborne pathogen including a *cryptosporidium parvum* virus being in low concentration, using the modified flow-type SPR sensor system, compared to the microorganism detection method using the conventional flow-type SPR sensor system.

The invention has been described using preferred exemplary embodiments. However, it is to be understood that the scope of the invention is not limited to the disclosed embodiments. On the contrary, the scope of the invention is intended to include various modifications and alternative arrangements within the capabilities of persons skilled in the art using presently known or future technologies and equivalents. The scope of the claims, therefore, should be accorded the broadest interpretation so as to encompass all such modifications and similar arrangements.

What is claimed is:

1. A method of detecting a pathogenic microorganism in real-time, using a flow-type surface plasmon resonance (SPR) biosensor, comprising steps of:
   i) performing an immune reaction of a pathogenic microorganism with an antibody thereto in a batch type;

ii) selectively separating the pathogenic microorganism bound with the antibody; and iii) binding, in real-time, the pathogenic microorganism bound with the antibody on a binding surface of a chip of a flow-type SPR sensor system.

2. The method according to claim 1, wherein the antibody is specific to the pathogenic microorganism and is bound with biotin.

3. The method according to claim 1, wherein the step of selectively separating the pathogenic microorganism bound with the antibody is performed using a cut-off membrane filter.

4. The method according to claim 2, further comprising continuously injecting streptavidin so that a streptavidin layer is formed on the binding surface of the chip of the flow-type SPR sensor system.

5. The method according to claim 4, wherein the pathogenic microorganism bound with the antibody is bound with the streptavidin layer on the binding surface of the chip of the flow-type SPR sensor system through a biotin-streptavidin reaction.

6. The method according to claim 5, wherein SPR signals, which are generated on the binding surface of the chip of the flow-type SPR sensor system, are continuously collected in real-time to detect the pathogenic microorganism.

7. The method according to claim 3, further comprising changing conditions of the immune reaction and conditions of the cut-off membrane filter, depending on the pathogenic microorganism to be detected.

8. The method according to claim 3, further comprising changing conditions of the immune reaction of the pathogenic microorganism with the antibody and conditions of the cut-off membrane filter, depending on the pathogenic microorganism to be detected.

9. The method according to claim 1, wherein the chip of the flow-type SPR biosensor system comprises a surface with a gold thin film for SPR measurement.

10. The method according to claim 9, wherein a self assembled monolayer of a thiol terminated group (—SH) is formed on the sold thin film, and a ligand is fixed on the self assembled monolayer being formed.

11. The method according to claim 10, wherein the ligand is streptavidin.

12. The method according to claim 1, wherein the pathogenic microorganism is a waterborne pathogen.

13. The method according to claim 12, wherein the waterborne pathogen is a *cryptosporidium parvum* virus.

14. The method according to claim 1, wherein the pathogenic microorganism is a pathogenic virus.

15. The method according to claim 14, wherein the pathogenic virus is selected from any one of the group consisting of a herpes virus, a pox virus, a hepatitis virus, a picorna virus, a rota virus, an influenza virus, a paramyxo virus, a rubella virus, a rabies virus, a slow virus, an onco virus, and an HIV virus.

* * * * *